(12) United States Patent
Prasad

(10) Patent No.: US 9,655,926 B1
(45) Date of Patent: May 23, 2017

(54) TREATMENT FOR HAIR THINNING AND HAIR LOSS

(71) Applicant: Amiya Prasad, New York, NY (US)

(72) Inventor: Amiya Prasad, New York, NY (US)

(73) Assignee: Amiya Prasad, New York, NY (US)

( * ) Notice: Subject to any disclaimer, the term of this patent is extended or adjusted under 35 U.S.C. 154(b) by 97 days.

(21) Appl. No.: 14/465,480

(22) Filed: Aug. 21, 2014

Related U.S. Application Data

(60) Provisional application No. 61/869,335, filed on Aug. 23, 2013.

(51) Int. Cl.
| | | |
|---|---|---|
| A61K 35/22 | (2015.01) | |
| A61K 47/46 | (2006.01) | |
| A61K 31/593 | (2006.01) | |
| A61M 37/00 | (2006.01) | |

(52) U.S. Cl.
CPC ............ *A61K 35/22* (2013.01); *A61K 31/593* (2013.01); *A61K 47/46* (2013.01); *A61M 37/00* (2013.01); *A61M 37/0015* (2013.01); *A61M 2037/0007* (2013.01); *A61M 2037/0023* (2013.01); *A61M 2037/0061* (2013.01)

(58) Field of Classification Search
CPC ...... A61Q 7/00; A61K 38/00; A61M 37/0015
See application file for complete search history.

(56) References Cited

U.S. PATENT DOCUMENTS

| | | | |
|---|---|---|---|
| 6,113,567 A * | 9/2000 | Becker | A61F 9/00772 |
| | | | 427/489 |
| 6,579,538 B1 | 6/2003 | Spievack | |
| 6,783,776 B2 | 8/2004 | Spievack | |
| 6,849,273 B2 | 2/2005 | Spievack | |
| 6,852,339 B2 | 2/2005 | Spievack | |
| 6,861,074 B2 | 3/2005 | Spievack | |
| 6,869,619 B2 | 3/2005 | Spievack | |
| 6,887,495 B2 | 5/2005 | Spievack | |
| 6,890,562 B2 | 5/2005 | Spievack | |
| 6,890,563 B2 | 5/2005 | Spievack | |
| 6,890,564 B2 | 5/2005 | Spievack | |
| 6,893,666 B2 | 5/2005 | Spievack | |
| 6,918,396 B1 | 7/2005 | Badylak et al. | |
| 8,420,106 B1 | 4/2013 | Binder | |
| 2003/0023283 A1* | 1/2003 | McDaniel | A61K 8/02 |
| | | | 607/88 |
| 2004/0034341 A1* | 2/2004 | Altshuler | A61B 18/203 |
| | | | 606/3 |
| 2007/0118059 A1* | 5/2007 | Luo | A61H 15/00 |
| | | | 601/86 |
| 2008/0138324 A1* | 6/2008 | Kleinsek | A61K 38/1808 |
| | | | 424/93.7 |

FOREIGN PATENT DOCUMENTS

| | | | | |
|---|---|---|---|---|
| CH | WO 2013007308 A1 * | 1/2013 | ............ A61K 8/983 | |
| EP | 1239897 B1 | 3/2004 | | |
| EP | 1428540 A1 | 6/2004 | | |
| EP | 1749543 A1 | 7/2007 | | |
| EP | 1135094 B1 | 11/2009 | | |
| WO | WO 2013013042 A1 | 1/2013 | | |
| WO | WO 2014047246 A1 * | 3/2014 | ............ A61K 35/12 | |

OTHER PUBLICATIONS

Hitzig, Gary. "Use of Urinary Bladder Matrix, a Bioactive, Acellular Scaffold, in Transplant Donor Scars and Androgenetic Alopecia: Initial Clinical Experience." American Journal of Cosmetic Surgery 29.1 (2012): 11-18.*

Nusbaum, B. P. (2004). Techniques to Reduce Pain Associated with Hair Transplantation. American journal of clinical dermatology, 5(1), 9-15.*

Amoh, Y. (Feb. 2009), "Multipotent nestin-expressing hair follicle stem cells." The Journal of Dermatology. [On-line.] 36 pp. 1-9. Available: doi: 10.1111/j.1346-8138.2008.00578.x [Jun. 2013].

Cotsarelis G (2006), "Epithelial stem cells: a folliculocentric view", J. Invest, Dermatol. 126 (7): 1459-68. doi:10.1038/sj.jid.5700376. PMID 16778814.

Ma DR, Yang EN, Lee ST (2004). "A review: the location, molecular characterisation and multipotency of hair follicle epidermal stem cells", Ann. Acad. Med. Singap. 33 (6): 784-8.PMID 15608839.

Ohyarna M., "Hair follicle bulge: a fascinating reservoir of epithelial stem cells." J Dermatol Sci. May 2007;46(2):81-9. Epub Jan. 5, 2007.

Paus R, Cotsarelis G (Aug. 1999). "The biology of hair follicles". N. Engl. J. Med. 341 (7): 491-7. doi:10.1056/NEJM199908123410706. PMID 10441606.

Conger, Krista (Apr. 2013) "The Secret Life of Hair Follicles Revealed by Stanford Researchers" Scope [ On-line] http://scopeblog.stanford.edu/2013/04/19/the-secret-life-of-hair-follicles-revealed-by-stanford-researchers/ [Jun. 2013].

Lander, Elliot "Cell Surgical Network" http://www.stemcellrevolution.com/currently-studying/hair-restoration/hair-restoration/ , [Jun. 2013].

Sclafani, M.D., Anthony P. "Induction of dermal collagenesis, angiogenesis, and adipogenesis in human skin by injection of platelet rich fibrin matrix", Archives of Facial Plastic Surgery—published online Oct. 17, 2011.

Okabe, et al., "Injectable soft-tissue augmentation by tissue engineering and regenerative medicine with human mesenchymal stromal cells, platelet-rich plasma and hyaluronic add scaffolds", Cytotherapy. 2009;11(3):307-16. doi: 10.1080/14653240902824773.

(Continued)

*Primary Examiner* — Bhisma Mehta
*Assistant Examiner* — Nilay Shah
(74) *Attorney, Agent, or Firm* — Davidson, Davidson and Kappel, LLC

(57) ABSTRACT

A process to increase hair growth and hair caliber which uses stem cells derived from acellular extracellular matrix, e.g., from urinary bladder and is combined with a nutrient rich medium of autologously harvested platelet rich plasma has been developed. Preferably, a microneedling device is used to induce "micro wounds" aids in the healing process of the hair bearing skin by converting the stem cells in the matrix to progenitor cells.

19 Claims, No Drawings

(56) References Cited

OTHER PUBLICATIONS

Cervelli, et al., "Use of platelet-rich plasma and hyaluronic acid in the loss of substance with bone exposure", Adv Skin Wound Care. Apr. 2011;24(4):176-81. doi: 0.1097/01.ASW.0000396302.05959.d3.

Gaber, et.al., "Effect of various methods of platelet-rich plasma gel preparation on transforming growth factor-β1 release", 2011 http://journals,lww.com/eaoms/Fulltext/2011/04000/Effect_of_various_methods_of_platelet_rich_plasma.4.aspx.

D. H. Kim, et al., "Successful Treatment of Alopecia Areata with Topical Calcipotriol", Ann Dermatol vol. 24, No. 3, 2012, http://dx.doi.org/10.5021/ad.2012.24.3.341.

I. Aoi, et al., "Vitamin D3 Modulates Hair Induction by DPCs" Stems Cells Transitional Medicine pp. 615-619 (Jun. 2012), doi: http://stemcellstm.alphamedpress.org/content/1/8/615.

Harold Silva, Irina M. Conboy Aging and Stem Cell Renewal,http://www.stembook.org/node/459, Jul. 7, 2013, Department of Bioengineering, University of California, Berkeley, California.

Dermaroller medical distributed by dermaroller US (see, www.dermarollerus.com) Jul. 21, 2012.

Gary Hitzig "Use of Urinary Bladder Matrix, a Bioactive, Acellular Scaffold, in Transplant Donor Scars and Androgenetic Alopecia: Initial Clinical Experience." American Journal of Cosmetic Surgery: Mar. 2012, vol. 29, No. 1, pp. 11-18. doi: http://dx.doi.org/10.5992/AJCS-D-11-00016.1.

Takikawa, M., et al.,"Enhanced Effect of Platelet-Rich Plasma Containing a New Carrier on Hair Growth." Dermatologic Surgery, 37: 1721-1729. doi: 10.1111/j.1524-4725.2011.02123.x Dec. 2011.

V. Cervelli MD, L. Lucarini, MD, D. Spallone, L. Brinci, and B. de Angelis, "Use of platelet rich plasma and hyaluronic acid on exposed tendons of the foot and ankle." Journal of Wound Care 2010 19:5, 186-190.

Cervelli, V., et al, "Use of autologous platelet rich plasma (A-PRP®) and hyaluronic acid on exposed tendons of the foot and ankle" Regen Lab SA, Switzerland, 1 page, 2014.

Sibbald "Special considerations in wound bed preparation 2011: an update©." Adv Skin Wound Care. Sep. 2011;24(9):415-36; quiz 437-8. doi: 10.1097/01.ASW.0000405216.27050.97.

Garza, LA, et al. "Bald scalp in men with androgenetic alopecia retains hair follicle stem cells but lacks CD200-rich and CD34-positive hair follicle progenitor cells." J Clin Invest. Feb. 2011;121(2):613-22. doi: 10.1172/JCI44478. Epub Jan. 4, 2011.

\* cited by examiner

TREATMENT FOR HAIR THINNING AND HAIR LOSS

BACKGROUND

The invention is a method for treating hair thinning and loss in mammals comprising using acellular extracellular matrix mixed with autologously harvested platelet rich plasma and other additives.

Hair loss on the scalp is a problem that has affected men and some women for generations. The most common type of hair loss in men is male pattern baldness or androgenetic alopecia. Usually with androgenetic alopecia, hair loss happens gradually over years starting from the crown of the head and in the frontal region of the scalp. For women suffering with hair loss, there is a thinning effect that is more spread out throughout the scalp and is more common after menopause. There are 2 medical treatments for hair loss in men, topical minoxidil and oral finasteride. For women, there is only topical minoxidil.

Thinning hair and hair loss have been the scourge of mankind for many years. Although many take it as an inevitable sign of aging, there are some people who are astounded to learn that in an age of modern medical miracles, there is no realistic answer for this problem. Hair loss and thinning is quite damaging to the ego for men and women. There are numerous socio-anthropological studies which show that men who have hair loss are seen as less competent, less energetic and less productive. Consequently, there are many men and women with thinning hair who thus significantly decrease their earning potential. Lower revenue or change of career in midlife are the choices that an individual often settles for because of an external physical change.

Androgenetic alopecia is the most common cause of hair loss affecting 50% of men and 20% to 53% of women by 50 years of age. This patterned form of hair loss is caused by genetic and hormonal factors and occurs in a highly predictable fashion in men and is more diffusely and less patterned in women. Hair transplantation is effective in replacing terminal hair follicles in hair loss areas. While this procedure is generally effective, the challenge for patients with severe hair loss is depletion of donor follicles before the area of hair loss is fully covered. Scar formation at the donor site can also occur. Therefore, the ability to remove hair from one area and transplant into another, while allowing the donor hair to grow back would be highly useful, as would the ability to reduce the incidence of donor scars, which are typically refractory to surgical excision. While researchers continue to make progress in this area, no treatment to date has emerged to eliminate donor scars completely or regenerate hair follicles in both the donor site or on the bald scalp.

OBJECTS AND SUMMARY

It is an object of the present invention to slow down or halt hair thinning in men and/or women.

It is a further object of the present invention to slow down, halt, restore or reverse thinning hair in men and/or women using acellular extracellular matrix administered to multiple levels of the skin and the fatty layer of tissue under the skin.

It is a further object of the present invention to slow down, halt, restore or reverse thinning hair in men and/or women using platelet rich plasma administered to multiple levels of the skin and the fatty layer of tissue under the skin.

It is a further object of the present invention to slow down, halt, restore or reverse thinning hair in men and/or women using acellular extracellular matrix combined with platelet rich plasma or other media as well as other additives administered to multiple levels of the skin and the fatty layer of tissue under the skin.

In accordance with the above objects and others, the present invention is directed in part to a process to increase hair growth and hair caliber comprising applying stem cells derived from acellular extracellular matrix suspended in a carrier selected from platelet rich plasma (e.g., autologously harvested platelet rich plasma), saline, albumin or hyaluronic acid or any other medium that encourages the particular stem cell's proliferation in the scalp such that hair growth as seen by increased density and caliber of the individual hairs results.

In certain preferred embodiments, the acellular matrix containing stem cells may be derived from urinary bladder, e.g., porcine-derived urinary bladder extracellular matrix (ECM).

In further preferred embodiments, the ECM is combined with a nutrient rich medium of autologously harvested platelet rich plasma.

The invention is further directed to a method of treating hair thinning or hair loss in mammals, comprising using a microneedling device, a derma pen or simple injections on the affected area of the scalp of a mammalian patient to create a microinjury at the fatty cell layer and dermal papilla cell (equivalent depths greater than 2 mm) and the bulge area (depth of approximately 1.8 mm); and administering a hair growth suspension comprising urinary bladder extracellular matrix, platelet rich plasma, and optionally Vitamin D on the affected area of the scalp of the patient. In certain preferred embodiments, the mammal is human. In certain preferred embodiments, the method further comprises utilizing a small massaging tool wrapped in protective cover and placed near needle insertion points on the scalp to diffusely distribute the injected hair growth suspension. In additional preferred embodiments, the hair growth suspension comprises from about 6 mL to about 15 mL of urinary bladder extracellular matrix, from about 2 mL to about 3 mL of the platelet rich plasma, and from about 1 mcg to about 2 mcg of Vitamin D. Certain preferred embodiments further comprise administering an effective amount of a corticosteroid to the scalp prior to administering the hair growth suspension in order to minimize inflammation.

The invention is further directed in part to a method of treating hair thinning or hair loss in mammals, comprising drawing blood from a patient who is to be treated for hair thinning or hair loss and centrifuging the blood to obtain platelet rich plasma; preparing a hair growth suspension comprising from about 100 mg to about 120 mg of porcine-derived fine particulate powder urinary bladder extracellular matrix such as MatriStem MicroMatrix Micronized Particles, Fine (100 mg vial), from a total volume of about 6 mL to about 15 mL (preferably about 10 mL) of PRP which is mixed with the urinary bladder extracellular matrix using aliquots of about 2 mL to about 3 mL (preferably about 2.5 mL) of the platelet rich plasma, and optionally from about 1.0 mL (1 mcg/mL) to about 2 mL of Vitamin D, and drawing from about 1.5 mL to about 3 mL of the suspension into at least one syringe with a blunt needle after mixing the suspension well; performing a ring block on the scalp of the patient using an effective amount of a local anesthetic; utilizing a small massaging tool wrapped in protective cover and placed near the needle to help lessen the pain of the injection; testing numbed areas of the scalp with a needle to ensure that the entire area to be injected is numb; adding additional injections of local anesthetic as needed based on feedback from the patient; administering the hair growth suspension of about 0.05 mL to about 0.3 or 0.4 mL per square centimeter in the thinnest or hair loss affected areas of the scalp at intervals from about 1 cm to about 2 cm; administering smaller amounts of the hair growth suspension to progressively thicker areas of the scalp, such that a total of from about 7.5 mL to about 10 mL of hair growth suspension is administered in total to the scalp of the patient; and utilizing a small massaging tool wrapped in protective cover and placed near needle insertion points on the scalp to diffusely distribute the injected hair growth suspension. In certain preferred embodiments, the method of claim further comprises administering an effective amount of a corticosteroid to the scalp prior to administering the hair growth suspension in order to minimize inflammation. In other preferred embodiments, the corticosteroid comprises about 3 mL triamcinolone (e.g., 4 mg/mL) and is administered as a total of about 30 to about 60 subcutaneous injections, each in an amount from about 0.05 to about 0.1 mL at intervals from about 1 to about 2 cm. In still other preferred embodiments, the corticosteroid comprises from about 6 mg to about 18 mg of triamcinolone.

In certain preferred embodiments, the total dose of hair growth suspension is administered in about 4 separate syringes having a blunt end, each of the syringes containing from about 0.05 mL to about 0.3 or 0.4 mL of hair growth suspension. In further embodiments, the method further comprises utilizing a microneedling device, a derma pen or simple injections on the affected area of the scalp of the patient prior to the administration of the hair growth material to the patient. In such embodiments, an effective amount of a corticosteroid is preferably administered to the scalp prior to administering the hair growth suspension in order to minimize inflammation. The corticosteroid may be, e.g., dexamethasone or betamethasone in an amount from about 4 mg to about 8 mg, and is administered within 2 hours before the micro--needling process begins.

The invention is further directed to the use of a microneedling device to induce "micro wounds", which aids in the healing process of the hair bearing skin by converting the stem cells in the matrix to progenitor cells. These progenitor cells will protect the hair follicles from dihydrotesterone and brings about hair growth in thinning areas as measured qualitatively, e.g., by high definition photos taken at 2 weeks, 1 month, 2 months, 6 months and 1 year.

In certain preferred embodiments, the invention is further directed in part to the use of fractional micro-needling medical devices to create "microwounds" that achieve a customized depth of administration as well as density of "microwounds," A commercially available micro-needling device, Dermapen®, has been found to work optimally by customizing its use according to the individual's pattern of hair loss. For patients with male pattern hair loss and fine individual baseline hair quality as well as thin scalp skin as determined by age over 45 or Fitzpatrick scale type 1 or type 2, the Dermapen will be set at mid dermal depths at about 1.5 to about 2 mm (mid to deep dermal) of about 35 microwounds per square cm to about 1000 microwounds per square cm. For male pattern hair loss in patients with baseline coarse hair and thicker scalp skin a depth of about 2 to about 2.5 mm to reach the dermal papilla is used to create effective microwounds. For female patients with Androgenetic pattern (male patter)), the mid dermal depth of about 1.5 to about 2.0 mm will be used but it will be limited to the temporal peak areas to prevent potential shedding which has been observed in some women. For pure female hair loss, the micro-needling device may be avoided altogether in certain embodiments. These microwounds optimally stimulate progenitor cells to achieve a wound healing response to convert adult stem cells and miniaturized hair follicles into active hair follicles. In addition, these "microwounds" serve as conduits for topically applied mixtures of acellular extracellular matrix to be delivered to the affected areas of skin.

The invention is further directed to the use of a urinary bladder extracellular matrix (ECM) for manufacture of a medicament for treatment of hair thinning and hair loss caused by conditions such as male pattern hair loss, female pattern hair loss, alopecia areata, traction alopecia and autoimmune conditions such as lupus erythematosus by delivery of a therapeutically effective amount of the ECM in a pharmaceutically safe form to the skin of a mammal (e.g., human).

In another embodiment, the invention is further directed to the use of urinary bladder extracellular matrix for manufacture of a medicament for other types of alopecia such as chemotherapy induced, alopecia universalis, alopecia totalis for treatment of hair thinning and hair loss in a mammal (e.g., human) by delivery of a therapeutically effective amount of the acellular matrix in a pharmaceutically safe form to the skin of the mammal.

In another embodiment, the invention is further directed to the use of adjuvants as catalysts to promote the activation of adult stem cells to stimulate progenitor cells for treatment of hair thinning and hair loss in a mammal by delivery of a therapeutically effective amount of the acellular matrix in a pharmaceutically safe form to the skin of the mammal. These adjuvants include, but are not limited to autologously harvested platelet rich plasma (PRP), calcitriol or Vitamin D3, betamethasone and other steroids to minimize inflammatory reactions to be used in doses as required by a particular human patient.

The invention is further directed in part to the use of specific fractional micro-needling medical devices to create "microwounds" that are necessary to achieve a customized depth of administration as well as density of microwounds to stimulate progenitor cells to achieve a wound healing response to convert adult stem cells and miniaturized hair follicles into active hair follicles and as conduits for topically applied mixtures of acellular extracellular matrix to be delivered to the affected areas of skin, Activation of adult stem cells and recruitment of progenitor cells in the presence of extracellular matrix, platelet rich plasma and other adjuvants will activate the hair follicles in areas of hair thinning to bear thicker hair and to duplicate hair follicles resulting in increased density and caliber of hairs in specific regions.

The invention is further directed to a kit for use in treating hair thinning or hair loss in mammals, comprising (i) Blood draw materials comprising a tourniquet, a butterfly, a vacutainer, four (4) Blood Collection Tube, Plasma, Lithium Heparin with gel separator, tubes (e.g., 8 mL); corticosteroid (e.g., dexamethasone), saline, needle (e.g., 20 gauge), luer lock syringe (e.g., 5 cc), and alcohol preps; (ii) a hair growth suspension comprising effective amounts of porcine-derived urinary bladder extracellular matrix (ECM), platelet rich plasma (PRP), two (2) Multidose adapters; and four (4) luer lock syringes (e.g., 3 cc each); and (iii) an effective amount of local anesthetic(s) materials. In certain preferred embodiments of the kit, the local anesthetic materials preferably comprise vials containing (i) Lidocaine 1%; (ii) Lidocaine 1% with epinephrine 1:100,000; (iii) bupivacaine 0.5%; and (iv) Betamethasone 10% (concentration), two (2) 10 cc syringes; two (2) 20 gauge needles; two (2) 30 gauge needles; and two (2) 25 gauge needles. In other embodiments, the hair growth suspension is contained in a vial (e.g., 100 mg).

DETAILED DESCRIPTION

The invention is a method for treating hair loss in mammals. This invention is a method for reduction of hair loss and stimulation of hair growth on the scalp of a human patient.

The use of the hair growth suspension prepared in accordance with the present invention can be used to treat typical male pattern baldness, typical female baldness, as well as other types of alopecia such as chemotherapy induced, alopecia universalis, alopecia totalis for treatment of hair thinning and hair loss in a mammal. This is accomplished, e.g., by delivery of a therapeutically effective amount of acellular matrix in a pharmaceutically safe form to the skin of the mammal (e.g., human).

The hair growth suspension which is used in the present invention and in the process described herein comprises one or more of a stem cell preparation or acellular matrix, platelet-rich plasma, and optional additional customized adjuvants such as Betamethasone or calcitriol.

The hair growth suspension preferably includes stem cells of non-embryonic origin that are optimized for growth in an appropriate medium including platelet rich plasma (e.g., autologously harvested platelet rich plasma), saline, albumin or hyaluronic acid or any other medium that encourages the particular stem cell's proliferation in the scalp such that hair growth as seen by increased density and caliber of the individual hairs results. Stem cells currently have numerous origins including subcutaneous fat, adipose derived stem cells, bulge cells from hair follicles, certain hematopoietic cells, and the matrix between cells of a variety of organs. The process of the present invention preferably includes these cells and uses the best medium for proliferation in order to promote hair growth, hair thickening and minimal scarring during a hair transplantation procedure.

The hair growth suspension in certain preferred embodiments includes adjuvants as catalysts to promote the activation of adult stem cells to stimulate progenitor cells for treatment of hair thinning and hair loss in a mammal by delivery of a therapeutically effective amount of the acellular matrix in a pharmaceutically safe form to the skin of the mammal. These adjuvants include, but are not limited to calcitriol or Vitamin D3, epinephrine 1:1000 or 1:10,000 or betamethasone and other steroids to minimize inflammatory reactions to be used in doses as specified by internally derived algorithms.

In the present invention, acellular extracellular matrix derived from (e.g., porcine) bladder is preferably combined with platelet rich plasma as a nutrient rich medium to nourish adult stem cells for slowing down, halting, restoring (regrowth of hair) or reversing thinning hair. Acellular extracellular matrix has been used in the armed forces and other settings for wound healing where the results have been remarkable for patients who suffered injuries from loss of a finger or loss of skin. The acellular extracellular matrix appears to work on dormant adult stem cells and calls over "progenitor" cells which have multipotent capabilities. During hair loss, the progenitor cells no longer protect the hair follicles from the damage induced by dihydrotestosterone (DHT), a hormone normally found in the body, which is most often responsible for hair loss. Although not wishing to be hound by this theory, it is hypothesized that when the acellular extracellular matrix is placed in a site of injury of hair bearing skin, the healing process of the area appears to revert the progenitor cells back to their role of protecting the hair follicle from the injuries caused by DHT. This results in thickening the hair and prevents thinning and eventual follicular death. In addition, the progenitor cells can duplicate hair follicles in the region.

Female pattern hair loss is seen fairly frequently with about 30% of women who are affected under the age of 50 and 50% is see over the age of 50. Although female pattern hair loss is common in females, its pathogenesis is poorly understood. Current medical thinking hypothesizes an unknown inflammatory process. Use of the acellular, extracellular mixture combined with platelet rich plasma has shown remarkable improvement. Counseling of such patients reveals that other medical factors may be involved in the hair loss so appropriate customized adjuvants may be added.

The method preferably administers acellular extracellular matrix preferably derived from urinary bladder (e.g., porcine) into the scalp of the patient in specific, customized according to hair loss, amounts with other materials to provide a therapeutically-effective restoration of hair growth. The result is the activation of adult stem cells to stimulate progenitor cells that will cause hair-growth without affecting any tissue not outside the skull of the patient. The method is performed by delivering acellular extracellular matrix in a nutrient rich medium such as platelet rich plasma (PRP) harvested autologously as well as other adjuvants in clinically appropriate doses according to specific algorithms particularly derived for hair loss, to a mammal topically, intracutaneously and subcutaneously at sites of hair thinning and hair loss. The preferred acellular extracellular matrix administered according to the invention is derived from porcine urinary bladder basement membrane that is known to produce adult stem cell activation for wound healing in multiple tissues in mammals.

Preferably, the hair growth suspension includes stem cells derived from acellular matrix. The acellular matrix useful in the present invention is known to those skilled in the art and is described, e.g., in U.S. Pat. Nos. 6,579,538; 6,783,776; 6,849,273; 6,852,339; 6,861,074; 6,869,619; 6,887,495; 6,890,562; 6,890,563; 6,890,564; 6,893,666; and 6,918,396, all of which are hereby incorporated by reference. Stem cells are further described in the following publications, all of which are hereby incorporated by reference: AMOH, Y. (2009, February), "Multipotent nestin-expressing hair follicle stem cells." The Journal of Dermatology. [On-line.] 36 pp. 1-9. Available: doi: 10.1111/j.1346-8138.2008.00578.x [June 2013]; Cotsarelis G (2006). "Epithelial stem cells: a folliculocentric view". J. Invest. Dermatol. 126 (7): 1459-68. doi:10.1038/sj.jid.5700376. PMID 16778814; Ma D R, Yang E N, Lee S T (2004). "A review: the location, molecular characterisation and multipotency of hair follicle epidermal stem cells". Ann. Acad. Med. Singap. 33 (6): 784-8. PMID 15608839; J Dermatol Sci. 2007 May; 46(2):81-9. Epub 2007 Jan. 5; Paus R, Cotsarelis G (August 1999). "The biology of hair follicles". N. Engl. J. Med. 341 (7): 491-7. doi:10.1056/NEJM199908123410706. PMID 10441606; Conger, Krista (2013, April) "The Secret Life of Hair Follicles Revealed by Stanford Researchers" Scope [On-line] www.scopeblog.stanford.edu/2013/04/19/the-secret-life-of-hair-follicles-revealed-by-stanford-researchers [June 2013]; and Lander, Elliot "Cell Surgical Network" www-.stemcellrevolution.com/currently-studying/hair-restoration/hair-restoration, [June 2013].

While all tissues have an underlying extracellular matrix (ECM), only those from the urinary bladder, skin, the submucosa of the small intestine, and the pericardium have been used clinically. Urinary bladder ECM (UBM) is the only organ that has an intact epithelial basement membrane, the anatomic site for epithelial cell development and residence, and is preferred in certain embodiments. The porcine UBM product is preferably prepared using methods that preserve the basement membrane structure. The degradation of naturally occurring ECM has also been associated with release of growth factors and peptides, many of which have been shown to maintain bioactivity. The growth factors contained in UBM include vascular endothelial growth factor, basic fibroblast growth factor, epidermal growth factor, transforming growth factors alpha and beta 1, keratinocyte growth factor, bone morphogenic protein, insulin-like growth factor, hepatic growth factor, and platelet-derived growth factor. UBM is primarily composed of collagen I, II, III, IV, and VII and contains glycosaminoglycans, fibronectin, laminin, and elastin. These growth factors have been demonstrated to maintain bioactivity following UBM preparation. ECM scaffolds have been described as degradable reservoirs of naturally occurring growth factors. Porcine-derived urinary bladder extracellular matrix (MatriStem, Acell Inc, Columbia, Md.) is an FDA-cleared, resorbable bioscaffold material and in certain preferred embodiments is a preferred acellular extracellular matrix material for use in the present invention.

In certain preferred embodiments, the hair growth suspension further includes platelet rich plasma as a nutrient rich medium for the extracellular matrix. However, in other embodiments, the acellular extracellular matrix is suspended in a carrier selected from saline, sterile water, albumin, hyaluronic acid and combinations thereof.

The platelet rich plasma (PRP) that is used in the present invention is known to those skilled in the art and is described, e.g., in the following publications incorporated by reference: Anthony P. Sclafani, M.D., "Induction of dermal collagenesis, angiogenesis, and adipogenesis in human skin by injection of platelet rich fibrin matrix", Archives of Facial Plastic Surgery—published online Oct. 17, 2011; K. Okabe, et al., "Injectable soft-tissue augmentation by tissue engineering and regenerative medicine with human mesenchymal stromal cells, platelet-rich plasma and hyaluronic acid scaffolds", Cytotherapy. 2009; 11(3):307-16. doi: 10.1080/14653240902824773; V. Cervelli, et al., "Use of platelet-rich plasma and hyaluronic acid in the loss of substance with bone exposure", Adv Skin Wound Care. 2011 April; 24(4): 176-81. doi: 10.1097/01.ASW.0000396302.05959.d3; A. Gaber, et. al., "Effect of various methods of platelet-rich plasma gel preparation on transforming growth factor-$\beta 1$ release", www.journals.1ww.com/eaoms/Fulltext/2011/04000/Effect_of_various_methods_of_platelet_rich_plasma.4.aspx Platelet-rich plasma systems have been reported to generate a product with an elevated concentration of growth factors of, e.g., up to from about 80 to about 180 times the normal value. PRP material is commercially available, e.g., as RegenKit® Autologous Platelet-rich Plasma (A-PRP). This system aids in the separation of the patient's own blood components through the use of the RegenKit THT vacuum tube and clinical centrifuge. RegenKit THT A-PRP is designed to deliver an increased concentration of bioactive factors and proteins through the concentration of platelets from whole blood. Once the blood is drawn into the RegenKit THT vacuum tube it is then spun under centrifugation according to centrifuge operating instructions. The PRP prepared using the RegenKit THT is a platelet-rich plasma preparation with high platelet recovery and viability, a physiological level of leukocytes, and contains the entire plasma component of blood, which is rich in growth factors. The platelet-rich plasma is collected with syringes and can be mixed during application at the patient's point of care.

The hair growth suspension used in the present invention may also include an effective amount (concentration) of vitamin D, or analogues or derivatives thereof. Hair follicles are highly sensitive to hormones. Vitamin D is a hormone that is known to play a role in calcium homeostasis, immune regulation, and cell growth and differentiation. The active form of vitamin D, 1,25-dihydroxyvitamin D3, mediates its action by binding to specific vitamin D receptors (VDR) located in the nuclei of target cells, and it has been reported and demonstrated that VDR is strongly expressed in the key structures of human and murine hair follicles. A lack of VDR is associated with reduced epidermal differentiation and hair follicle growth, and the presence of VDR in keratinocytes is necessary for maintenance of the normal hair cycle. Accordingly, in certain preferred embodiments, the hair growth material used in the present invention may include vitamin D, an analogue thereof, a derivative thereof, or mixtures of any of the foregoing. Such materials may be particularly useful where the patient is suffering from alopecia areata, an inflammatory hair loss of unknown etiology. A particularly useful additive is calcipotriol, a strong vitamin D analog. The use of calcipotriol in hair loss is described, e.g., by D. H. Kim, et al., "Successful Treatment of Alopecia Areata with Topical Calcipotriol", Ann Dermatol Vol. 24, No. 3, 2012, www.dx.doi.org/10.5021/ad.2012.24.3.341 hereby incorporated by reference. The use of vitamin D3 is also described by I. Aoi, et al., "Vitamin D3 Modulates Hair Induction by DPCs" Stems Cells Transitional Medicine pp. 615-619 (June 2012), doi:www.stmcellstm.alphamedpress.org/content/1/8/615, hereby incorporated by reference.

In other preferred embodiments, the hair growth material used in the present invention includes a topical corticosteroid. Topical corticosteroids include but are not limited to Clobetasol, Betamethasone, Halobetasol, Diflorasone, Fluocinonide, Halcinonide, Amcinonide, Desoximetasone, Triamcinolone, Mometasone, Fluticasone, Betamethasone, Fluocinolone, Hydrocortisone, Flurandrenolide, Desonide, Alclometasone, and mixtures of any of the foregoing.

The preparation of the hair growth material may be accomplished as follows. The desired amount of PRP is prepared by drawing from about 24 mL to about 32 mLs of blood from the patient and then centrifuging the drawn blood at a speed from about 4000 RPM to about 5000 RPM for a time period from about 11 to about 15 minutes. The concentration of platelets varies from 220,000 platelets per microliter to 1, 000,000 platelets per microliter and will be used to treat the scalp of humans or an area of approximately 200 square centimeters (cm2) for mammals. Thereafter, the centrifuged product is removed from the centrifuge tubes with syringes and is added to the ECM fine particulate vial (e.g., MatriStem MicroMatrix 100 mg fine particulate powder, catalog number:mm0100F, commercially available from Acell, Columbia Md.). In certain embodiments, an amount of vitamin D from about 0.75 mL to about 1.0 mL (from about 0.75 mcg to about 1.0 mcg) known as Calcitriol 1.0 mcg/mL (available through AKORN located in Lake Forest, Ill.) is then added to the vial along with effective amounts of any other optional additives (based on the needs of the particular patient). The vial is then gently mixed by turning over to mix the ingredients into a suspended state). The suspension is then ready for use. It is preferably used immediately and should be discarded in about 1 hour.

In another embodiment, in the preparation of PRP, calcium chloride is added to the mixture. Calcium chloride increases the adhesive nature of the platelets which yields a thicker texture of the solution, rendering a more gel-like state. The advantage of this preparation is that the PRP is more likely to remain in an administered area of treatment rather than diffusing out to other areas.

The acellular extracellular matrix is available in a sterile, dry powder as well as sheets. It is reconstituted in specific concentrations. For example, about 100 mg of ACELL may be mixed with about 7.5 mL PRP to achieve a final concentration of about 13.33 mg ACELL/mL PRP. This concentration has been selected because it has demonstrated clinical improvement in our practice. If adjuvants are desired to be added to the acellular extracellular matrix, they are added to the syringe just before administration to the patient.

In certain embodiments, a preferred agent to be added to the extracellular matrix is a vitamin D product such as Calcitriol®, which may be added, e.g., at about 1.0 mcg/mL and is to be added to Acell 100 mg fine particulate powder before adding the nutrient medium of platelet rich plasma.

In additional preferred embodiments, together with or in substitution for the Vitamin D is added an anti-inflammatory steroid. For example, Kenalog® (10 mg/mL) may be added to the Acell 100 mg bottle directly in a volume of 1.5 mL which is a dose of 15 mg. Then 7.5 mL of platelet rich plasma is added to the bottle to make a total concentration of 11.1 mg Acell/mL of platelet rich plasma. In this case, 9 mL of volume will be delivered to the scalp so that the total dose of 100 mg Acell will still be delivered. In other embodiments, an anti-inflammatory steroid such as Kenalog® (10 mg/mL) is diluted to 5 mg/mL with sterile saline and then a total dose of 15 mg in a volume of 3 mL is then administered subcutaneously in approximately 0.1 to 0.3 mL aliquots in all areas of intended treatment.

Since it is believed that progenitor cells can be recruited from the fatty layer, the acellular extracellular matrix may be administered to multiple levels of the skin and the fatty layer of tissue under the skin (e.g., by subcutaneous injections). It is believed that the progenitor cells protect the follicle from the inflammation and help the hair thickening and re-growth process to restart. It is preferred then, that men and women who notice hair loss not ignore the signs, but instead, seek treatment to maximize their full hair growth potential. It has been found that the efficacy of the administration of the acellular extracellular matrix declines when the patient waits until they have experienced substantial hair loss. Based on clinical observations thus far, age of the patient matters as does amount of hair loss. It seems that younger patients possess more active stem cells and have faster wound healing. www.stembook.org/node/459, Jul. 7, 2013, Aging and Stem Cell Renewal, Haroldo Silva, Irina M. Conboy, Department of Bioengineering, University of California, Berkeley, Calif., hereby incorporated by reference.

It has been found that the hair growth suspension when administered in accordance with the present invention can slow down, halt, restore or reverse thinning hair in men and/or women in a single treatment to the affected area. However, the present invention contemplates that multiple treatments can be administered, even to the same affected area, should the need arise (e.g., the patient begins to experience balding in the treated area again after a period of time).

In preferred embodiments, a process which involves incorporating standards of medical sterility and analgesia as practiced in health care is utilized to administer the hair growth material of the present invention.

First, the patient's scalp is preferably prepped with an antibiotic wash.

Next, the patient is given a "ring block" which is a series of local anesthetic injections used in a circumferential pattern to completely numb the scalp. In certain preferred embodiments, the ring block is accomplished by injecting an effective amount of local anesthetic. Lidocaine and/or bupivacaine (which is a longer acting local anesthetic) are commonly used in the treatments of the present invention. In certain embodiments, a nerve block may also be administered in the area of the inside eyebrows to block the supraorbital and supratrochlear nerves.

Prior to the administration of the hair growth material to the patient, an IV injection of a corticosteroid is preferably administered. In certain preferred embodiments, an IV steroid (e.g., dexamethasone (Decadron®) or betamethasone) in an amount from about 4 mg to about 8 mg is administered, most preferably about 4 mg within 2 hours before the (optional) microneedling process begins. Microneedling is avoided in those patients whose hair loss may be secondary to an active inflammatory process. For a patient with alopecia areata, there may be an indication for microneedling but not in a female pattern hair loss.

Thereafter, in certain preferred embodiments betamethasone injection is then administered (4 mg/mL and total of 3 mL (12 mg) distributed over the entire scalp) subcutaneously throughout the area of hair thinning.

The patient's scalp is then preferably massaged using the technicians' fingers or a massager in order to improve distribution of the fluid and prevent dilution of the hair growth suspension In certain preferred embodiments, a vibration device such as the Brookstone mini usb personal massager is used.

The hair growth material (suspension) is then preferably drawn up into a suitable syringe with needle or blunt tip cannula with either a 15 g to 25 g needle or blunt cannula. The patient is then injected with the hair growth suspension described above, preferably in consistent volumes of 0.1 mL to 0.2 mL per square cm of thinning areas. Transition zones of thicker to thinning areas will get about 0.1 mL per square cm and thick areas considered to be genetically resistant to hair loss will not receive the injection. The depth of the injections is subcutaneous where research shows that source of stem cells is located so that a "wound healing" process may be initiated. In addition, injections are also performed in the intradermal level to initiate a similar response from stem cells located in areas of the hair follicle such as the "bulge" region.

In certain preferred embodiments, the total amount of suspension administered via subcutaneous injection to the scalp of the patient is from about 0.05 mL to about 0.1 mL per application and most preferably a total volume from about 9 mL to about 12 mL total volume. On average 9 mL are delivered subcutaneously. After the microneedling process, about 1 mL is delivered intradermally with a topical application of the hair suspension material.

In certain preferred embodiments, small "micro injuries" are created in the treatment area. In certain preferred embodiments, these micro injuries are created using a microneedling device such as the Dermapen Medical Model. Preferably, the 11 stainless steel micro needles are spaced at a distance from each other of from about 3.5 mm to about 4 mm. Preferably, the needles are from about 30 to about 33 gauge. The needles preferably pierce the skin of the scalp to a depth from about 0.25 to about 2.5 mm and have multiple speeds ranging from 1 (which is 25 holes per second) to 7 (which is about 1000 holes per second). The micro-needling process creates clusters of injuries. The use of specific fractional micro-needling medical devices to create "microwounds" achieve a customized depth of administration, from anywhere to superficial epidermal layer to deep dermal layers, as well as density of "microwounds". These microwounds optimally stimulate progenitor cells to achieve a wound healing response to convert adult stem cells and miniaturized hair follicles into active hair follicles. In addition, these "microwounds" serve as conduits for transdermal delivery of the mixture of acellular extracellular matrix and platelet rich plasma to be delivered to the affected areas of skin.

In other embodiments, another device is used to create clusters of injuries in the treatment area in addition to or instead of the micro-needling device. For example, a derma roller can be used, dermaroller medical distributed by dermaroller US (see, www.dermarollerus.com). Accordingly, the term "Dermapen" may be substituted with the term "micro-needling device" throughout this application.

In the present inventive method, the micro-needling device works best for male and female patients with male pattern hair loss. It has been determined that micro-needling device (e.g., Dermapen) use, especially with increased depth and number of microwounds and total coverage of affected areas actually enhanced the shedding of female patients with a female pattern of diffuse hair loss and it was determined that the micro-needling device was being used too "aggressively" and that an inflammatory component in female pattern hair loss was the explanation for early and diffuse shedding.

Recent articles showed that the activation of the hair growth cycle started by stimulating the hair growth response in two critical hair follicle areas—the dermal papilla and the bulge cell area.

In the present invention, this is accomplished by creating a microinjury, which has to be limited so as not to damage the hair growth process. This is accomplished by customizing the depth, the density and the frequency with which microwounds would be most effective. The hair growth process is dependent on functioning stem cells which communicate with the dermal papilla and the bulge area. Signals from the fatty cell layer are sent to the dermal papilla which then communicate with the bulge cells and start the hair growth cycle. Our aim is therefore to create a microinjury at the fatty cell layer and dermal papilla cell (equivalent depths greater than 2 mm) and the bulge area (depth of approximately 1.8 mm). This customized protocol yields more predictable and consistent results in hair regrowth.

In yet further alternative embodiments, micro injuries are created in the treatment area via the use of needles, only without a micro-needling device.

In other embodiments, a different depth of injection is used since damage to the bulge cells in the hair follicle has resulted in recruitment of progenitor cells—the depth for intradermal is about 0.5 mm.

Activation of adult stem cells and recruitment of progenitor cells in the presence of extracellular matrix, platelet rich plasma and other adjuvants will activate the hair follicles in areas of hair thinning to bear thicker hair and to duplicate hair follicles resulting in increased density and caliber of hairs in specific regions.

In certain preferred embodiments, a small local massager is also utilized in the treatment area to help decrease any potential pain experienced by the patient during the treatment process using the Gate Control theory of mechanical stimulation to lessen the stimulation of the nociceptors or pain fibers. The Brookstone mini usb personal massager will also help with better distribution of the suspension as well.

In certain preferred embodiments, a small amount of platelet rich plasma (e.g., from about 2 to about 3 mL) is applied to the scalp topically after the suspension injections and micro-needling steps are completed and a local massager is used again for analgesia purposes. The massage is preferably performed throughout the scalp area and around the ears.

The scalp is cleaned and the patient's hair is dried. The patient's scalp is then cared for appropriately after the procedure, preferably with follow-up examinations (e.g., 1 week after the treatment, and then 1 month, 6 months, 9 months and 1 year after the treatment).

The present invention also relates in part to a kit for use in the present invention. The kit advantageously will allow those having ordinary skill in the art to reduce errors, reduce risk of contamination, reduce waste, and reduce theft of disposable inventory. The kit preferably comprises (i) Blood draw materials; (ii) the ECM/PRP prep; and (iii) anesthetic(s). The blood draw materials preferably comprise a tourniquet, a butterfly, a vacutainer, four (4) Blood Collection Tube, Plasma, Lithium Heparin with gel separator, 8 mL tubes; corticosteroid (e.g., dexamethasone), saline, 20 gauge needle, 5 cc luer lock syringe, and alcohol preps. The ECM/PRP prep preferably contains ECM (extracellular matrix) 100 mg vial; two (2) Multidose adapters; and four (4) 3 cc luer lock syringes. The anesthetic materials preferably comprise vials containing (i) Lidocaine 1%; (ii) Lidocaine 1% with epinephrine 1:100,000; (iii) bupivacaine 0.5%; and (iv) Betamethasone 10% (concentrations). For topical anesthesia, the kit further preferably comprises two (2) 10 cc syringes; two (2) 20 gauge needles; two (2) 30 gauge needles; and two (2) 25 gauge needles.

DETAILED DESCRIPTION OF PREFERRED EMBODIMENTS

The following example represents specific embodiments of the foregoing discovery, and is not representative of the entire scope of the invention.

Example

A hair rescue treatment in accordance with the present invention basically utilizes a combination of ACELL, PRP and other factors. During the procedure, medical practitioners and technicians preferably wear surgical caps during the whole procedure and use clean gloves that are changed frequently. Standard precautions are utilized in order to avoid inadvertent needle sticks and contact with body fluids.

A treatment in accordance with the invention may utilize the following materials set forth in Table 1:

TABLE 1

1 Chuck
3 Pairs of Gloves (NO LATEX)
1 Isolation Gown
1 Safety Goggles
1 Tourniquet
1 Butterfly Needle
1 Vaccu
2 Alcohol Pads
1 Bandaid
4 GTHG Vials (Green Top Heparin/Gel Seperator)
5 15 g × 1½" Blunt Tip Cannulas TABLE 1-continued 4 3 CC Syringes
1 100 mg ACell The following preparations set forth in Table 2 may be utilized in the treatment:

TABLE 2

Topical Lidocaine Cream 2% with Epi
1 Vial of Decadron ® (ONLY DRAW 1 CC) [4 mg/CC]
1 Vial of Kenalog ® (ONlY DRAW 5 mL's) [mg/mL|Total 25 mg]
1 Vial of Lidocaine 1% Plain (ONLY DRAW 4 CC's)
1 Vial of Lidocaine with Epi (ONLY DRAW 4 CC's)
1 Vial of Marcaine ®0.25% (ONLY DRAW 1.5 CC's)
1 Vial of Sodium Bicarbonate 8.4% (ONLY DRAW 0.5 CC's)
2 5 CC Syringe
2 1 CC Syringe
4 22 g Needle
1 Massager
1 Protective Cover for Massager The following procedure is used:
1) Clean a level countertop with a cidex wipe.
2) Get a chuck and place the chuck on a level countertop.
3) Retrieve all supplies and place on chuck.
4) Place the tourniquet on the patients arm.
5) Using the butterfly needle, draw blood and fill 3 GTHG vials.
6) Infuse patient with 4 mg of Decadron® via IV or butteryfly.
7) Place 4 vials of blood in centrifuge. Spin at 4,000 RPM for 11 minutes.
8) Draw up 5 mL of Kenalog (final diluted concentration of 5 mg/mL) in a 5 CC syringe with a 22 g needle. PUT THE NEEDLE COVER ON. Place back on chuck.
9) Draw up 5 CC of Lidocaine 1% plain in a 5 CC syringe with a 22 g needle. PUT THE NEEDLE COVER ON. Place back on chuck.
10) Draw up 0.75 CC of Vitamin D in a 1 CC syringe with a 22 g needle. PUT THE NEED COVER ON. Remove needle carefully and discard in sharp's container Place back on chuck.
11) Once the blood is spun, remove and place the 4 GTHG test tubes in the test tube holder.
12) Using 1 3 CC syringe with a blunt needle for each green top test tube, draw out 3 cc of plasma. Repeat step for each test tube.
13) Open the ACell® Vial. Take each 3 CC syringe of plasma directly to the 100 mg of ACell vial (MatriStem MicroMatrix 100 mg fine particulate powder), deliver 2.5 cc of plasma. Place each syringe back on chuck
14) Add the 0.75 CC of Vitamin D to the ACell® vial.
15) Place the stopper tightly back on the ACell® vial.
16) Using the gloved index finger and thumb, cover the bottom and stopper and gently rock the vial 10 times in 1 direction. (a machine that rocks the vial is used)
17) Using the 3 CC syringe with blunt needle, slowly draw out 3 CC of ACell® mixture. Repeat step for each syringe. Place each syringe back on chuck.
18) A ring block is performed using a 5 CC syringe of Lidocaine (Plain: with NO Epinephrine) to numb the nerves in the scalp.
The following 6 sensory nerve branches of either the trigeminal nerve or the cervical nerve supply the scalp, and are numbed:

Supratrochlear nerve—A branch of the ophthalmic division of the trigeminal nerve; this nerve supplies the scalp in the medial plane at the frontal region, up to the vertex;

Supraorbital nerve—Also a branch of the ophthalmic division of the trigeminal nerve; this nerve supplies the scalp at the front, lateral to the supratrochlear nerve distribution, up to the vertex;

Zygomaticotemporal nerve—A branch of the maxillary division of the trigeminal nerve; it supplies the scalp over the temple region;

Auriculotemporal nerve—A branch of the mandibular division of the trigeminal nerve; it supplies the skin over the temporal region of the scalp;

Lesser occipital nerve—A branch of the cervical plexus (C2); it supplies the scalp over the lateral occipital region;

Greater occipital nerve—A branch of the posterior ramus of the second cervical nerve; it supplies the scalp in the median plane at the occipital region, up to the vertex.

19) A small massaging tool is wrapped in protective cover and placed near the needle to help lessen the pain of the injection. Test numbed areas with needle and make sure that the entire area to be injected is numb. Add small injections of Lidocaine as needed depending on the feedback from the patient
20) Using the 5 mL of Kenalog®, a total of approx. 50 SQ injections in 0.05 to 0.1 cc at 1-2 cm intervals on the scalp as a pre-treatment to minimize inflammation.
21) Begin the ACell® injections approximately 0.5 CC in the thinnest areas on the scalp approximately every 1 to 2 cm. Add to progressively thicker areas once the thinner areas are satisfactorily injected. Use ALL 4 syringes of ACell®.
22) A small massaging tool that is wrapped in protective cover and placed near the needle to help diffusely distribute the injections.
23) Use a spray bottle with water and clean and style hair as needed upon completion of injections.

CONCLUSION

It will be readily apparent to one of ordinary skill in the relevant arts that other suitable modifications and adaptations to the methods and applications described herein are suitable and may be made without departing from the scope of the invention or any embodiment thereof. While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims.

The invention claimed is:

1. A method for treating hair thinning or hair loss in mammals, comprising using a microneedling device, a derma pen or simple injections on an affected area of a scalp of a mammalian patient to create a microinjury at a fatty cell layer, at a dermal papilla cell and at a bulge area, with both the fatty cell layer and the dermal papilla cell having a depth greater than 2 mm and the bulge area having a depth of approximately 1.8 mm;

administering a hair growth suspension comprising urinary bladder extracellular matrix, platelet rich plasma, and Vitamin D on the affected area of the scalp of the patient, and wherein the hair growth suspension comprises about 6 mL to about 15 mL of urinary bladder extracellular matrix, about 2 mL to about 3 mL of the platelet rich plasma, and about 1 mcg to about 2 mcg of the Vitamin D.

2. The method of claim 1, further comprising administering an effective amount of a corticosteroid to the scalp prior to administering the hair growth suspension in order to minimize inflammation.

3. The method of claim 2, wherein the corticosteroid comprises about 6 mg to about 18 mg triamcinolone applied in solution and is administered as a total of about 30 to about 60 subcutaneous injections, each in an amount about 0.05 to about 0.1 mL at intervals about 1 cm to about 2 cm.

4. The method of claim 2, wherein the corticosteroid is dexamethasone or betamethasone in an amount about 4 mg to about 8 mg, and is administered within 2 hours before a microneedling process begins.

5. The method of claim 1, wherein at least one of the hair thinning and hair loss of the patient is caused by conditions such as male pattern hair loss, female pattern hair loss, alopecia areata, traction alopecia and autoimmune conditions such as lupus erythematosus.

6. The method of claim 1, wherein a total dose of the hair growth suspension is administered in about 4 separate syringes having a blunt end, each of the syringes containing about 0.05 mL to about 0.4 mL of the hair growth suspension.

7. A method for treating hair thinning or hair loss in mammals, comprising
drawing blood from a patient who is to be treated for hair thinning or hair loss and centrifuging the blood to obtain platelet rich plasma;
preparing a hair growth suspension comprising about 6 mL to about 15 mL of urinary bladder extracellular matrix, about 2 mL to about 3 mL of the platelet rich plasma, and Vitamin D, and drawing about 1.5 mL to about 3 mL of the suspension into at least one syringe with a blunt needle after properly mixing the suspension;
performing a ring block on a scalp of the patient using an effective amount of a local anesthetic;
utilizing a small massaging tool wrapped in protective cover and placing near the needle to numb an area where the hair growth suspension will be administered to help lessen pain from an injection;
testing numbed areas of the scalp with the needle or a different needle to ensure that the numbed area to be injected is numb;
adding additional injections of local anesthetic as needed based on feedback from the patient;
using a microneedling device, a derma pen or simple injections on an affected area of the scalp of the patient prior to an administration of the hair growth suspension to the patient, to create a microinjury at a fatty cell layer, at a dermal papilla cell and at a bulge area, with both the fatty cell layer and the dermal papilla cell having a depth greater than 2 mm and the bulge area having a depth of approximately 1.8 mm;
administering the hair growth suspension of about 0.5 mL in areas of the scalp that are thinnest at intervals about 1 cm to about 2 cm;
administering greater amounts of the hair growth suspension to progressively thicker areas of the scalp, such that a total of about 7.5 mL to about 10 mL of hair growth suspension is administered to the scalp of the patient; and
utilizing the small massaging tool wrapped in a protective cover and placed near the needle insertion points on the scalp to diffusely distribute the injected hair growth suspension.

8. The method of claim 7, further comprising administering an effective amount of a corticosteroid to the scalp prior to administering the hair growth suspension in order to minimize inflammation.

9. The method of claim 8, wherein the corticosteroid comprises about 6 mg to about 18 mg of a solution containing triamcinolone and is administered as a total of about 30 to about 60 subcutaneous injections, each in an amount about 0.05 to about 0.1 mL at intervals about 1 cm to about 2 cm.

10. The method of claim 7, wherein a total dose of the hair growth suspension is administered in about 4 separate syringes having a blunt end, each of the syringes containing about 0.05 mL to about 0.4 mL of the hair growth suspension.

11. The method of claim 10, further comprising administering an effective amount of a corticosteroid to the scalp prior to administering the hair growth suspension in order to minimize inflammation.

12. The method of claim 11, wherein the corticosteroid is dexamethasone or betamethasone in an amount of about 4 mg to about 8 mg, and is administered within 2 hours before a microneedling process begins.

13. The method of claim 7, wherein at least one of the hair thinning and hair loss of the patient is caused by conditions such as male pattern hair loss, female pattern hair loss, alopecia areata, traction alopecia and autoimmune conditions such as lupus erythematosus.

14. The method of claim 7, wherein the Vitamin D is in a range of about 1 mcg to about 2 mcg.

15. A method for treatment of hair thinning and hair loss, comprising delivering a therapeutically effective amount of hair growth suspension comprising a urinary bladder extracellular matrix material in a pharmaceutically acceptable form to a scalp of a human patient, wherein the hair growth suspension comprises about 6 mL to about 15 mL of the urinary bladder extracellular matrix, about 2 mL to about 3 mL of the platelet rich plasma, and about 1 mcg to about 2 mcg of Vitamin D.

16. The method of claim 15, wherein the urinary bladder extracellular matrix material is porcine urinary bladder extracellular matrix.

17. The method of claim 15, further comprising administering an effective amount of a corticosteroid to the scalp prior to administering the hair growth suspension in order to minimize inflammation.

18. The method of claim 17, wherein the corticosteroid comprises about 6 mg to about 18 mg triamcinolone applied in solution and is administered as a total of about 30 to about 60 subcutaneous injections, each in an amount about 0.05 to about 0.1 mL at intervals about 1 cm to about 2 cm.

19. The method of claim 15, wherein a total dose of the hair growth suspension is administered in about 4 separate syringes having a blunt end, each of the syringes containing about 0.05 mL to about 0.4 mL of the hair growth suspension.

* * * * *